United States Patent
Pionke et al.

(10) Patent No.: US 9,833,779 B2
(45) Date of Patent: Dec. 5, 2017

(54) METHODS, SYSTEMS, AND COMPUTER PROGRAM PRODUCTS FOR DETECTING PIPETTE TIP INTEGRITY

(71) Applicant: bioMerieux, Inc., Durham, NC (US)

(72) Inventors: Jeremey Joseph Pionke, O'Fallon, MO (US); Joel Patrick Harrison, Maryville, IL (US); Daniel Oliver Luebbert, St. Peters, MO (US); Daniel Joseph Pingel, St. Peters, MO (US)

(73) Assignee: bioMerieux, Inc., Durham, NC (US)

( * ) Notice: Subject to any disclaimer, the term of this patent is extended or adjusted under 35 U.S.C. 154(b) by 195 days.

(21) Appl. No.: 14/826,749

(22) Filed: Aug. 14, 2015

(65) Prior Publication Data

US 2016/0045911 A1 Feb. 18, 2016

Related U.S. Application Data

(60) Provisional application No. 62/037,659, filed on Aug. 15, 2014, provisional application No. 62/037,650, filed on Aug. 15, 2014, provisional application No. 62/037,652, filed on Aug. 15, 2014, provisional application No. 62/037,661, filed on Aug. 15, 2014.

(51) Int. Cl.
*B01L 3/02* (2006.01)
*G01N 35/10* (2006.01)
*G01N 35/00* (2006.01)

(52) U.S. Cl.
CPC ............. *B01L 3/0237* (2013.01); *B01L 3/021* (2013.01); *B01L 3/0275* (2013.01); *G01N 35/0099* (2013.01); *G01N 35/00623* (2013.01); *G01N 35/10* (2013.01); *G01N 35/1009* (2013.01); *B01L 3/0268* (2013.01); *B01L 2200/146* (2013.01); *B01L 2300/0627* (2013.01); *B01L 2300/0681* (2013.01); *B01L 2400/02* (2013.01); *G01N 2035/103* (2013.01); *G01N 2035/1018* (2013.01)

(58) Field of Classification Search
CPC ...... B01L 3/021; B01L 3/0275; B01L 3/0237; G01N 35/00623; G01N 35/0099; G01N 35/10; G01N 35/1009
See application file for complete search history.

(56) References Cited

U.S. PATENT DOCUMENTS

| | | | |
|---|---|---|---|
| 5,463,895 | A | 11/1995 | Brentz |
| 6,158,269 | A | 12/2000 | Dorenkott et al. |
| 6,213,354 | B1 | 4/2001 | Kay |
| 6,370,942 | B1 | 4/2002 | Dunfee et al. |
| 6,641,545 | B1 | 11/2003 | Colin et al. |

(Continued)

FOREIGN PATENT DOCUMENTS

| | | |
|---|---|---|
| EP | 2 561 929 A1 | 2/2013 |
| WO | WO 2012/045416 A1 | 4/2012 |
| WO | WO 2012/069925 A1 | 5/2012 |

OTHER PUBLICATIONS

International Search Report and the Written Opinion of the International Searching Authority corresponding to International Patent Application No. PCT/US2015/045304 (11 pages) (dated Oct. 22, 2015).

(Continued)

*Primary Examiner* — Paul West
(74) *Attorney, Agent, or Firm* — Myers Bigel, P.A.

(57) ABSTRACT

This invention relates to methods, systems, and computer program products for detecting pipette tip integrity.

20 Claims, 8 Drawing Sheets

(56) References Cited

U.S. PATENT DOCUMENTS

| | | |
|---|---|---|
| 7,171,316 B2 | 1/2007 | DeVries et al. |
| 7,502,695 B2 | 3/2009 | DeVries et al. |
| 7,634,378 B2 | 12/2009 | Kaplit |
| 7,694,591 B2 | 4/2010 | Leibfried |
| 7,799,574 B2 | 9/2010 | Saegusa |
| 7,867,769 B2 | 1/2011 | Dunfee et al. |
| 7,917,313 B2 | 3/2011 | Ziegler et al. |
| 7,926,325 B2 | 4/2011 | Kaplit |
| 7,941,285 B2 | 5/2011 | Devries et al. |
| 8,257,664 B2 | 9/2012 | Ogusu |
| 8,307,722 B2 | 11/2012 | Tajima et al. |
| 8,496,801 B2 | 7/2013 | Huang |
| 8,691,558 B2 | 4/2014 | Gupta et al. |
| 8,696,294 B2 | 4/2014 | Gupta et al. |
| 8,874,399 B2 | 10/2014 | Beumer et al. |
| 8,997,552 B2 | 4/2015 | Feldmann et al. |
| 9,097,607 B2 | 8/2015 | Izumo et al. |
| 9,500,665 B2 | 11/2016 | Fukuda et al. |
| 2002/0188410 A1 | 12/2002 | Salje |
| 2004/0149015 A1 | 8/2004 | Hansen et al. |
| 2007/0177986 A1 | 8/2007 | Leibfried |
| 2009/0070049 A1 | 3/2009 | Ziegler et al. |
| 2009/0075386 A1 | 3/2009 | Dunfee et al. |
| 2011/0104810 A1 | 5/2011 | Shiba et al. |
| 2013/0073243 A1 | 3/2013 | Beumer et al. |
| 2014/0137980 A1 | 5/2014 | Millet |
| 2014/0146642 A1 | 5/2014 | Ooi et al. |

OTHER PUBLICATIONS

U.S. Appl. No. 14/826,716, filed Aug. 14, 2015, Pingel et al.
U.S. Appl. No. 14/826,736, filed Aug. 14, 2015, Luebbert et al.
U.S. Appl. No. 14/826,767, filed Aug. 14, 2015, Luebbert et al.
PREVI® Isola Product Overview www.biomerieux-usa.com(2 pages) (2009).
"Tecan's Pressure Monitored Pipetting supports Swiss BioQuant's dedication to excellence" www.tecan.com(1 page) (Oct. 25, 2011).

METHODS, SYSTEMS, AND COMPUTER PROGRAM PRODUCTS FOR DETECTING PIPETTE TIP INTEGRITY

RELATED APPLICATION INFORMATION

This application claims the benefit of and priority to U.S. Provisional Application Ser. No. 62/037,659, filed Aug. 15, 2014, U.S. Provisional Application Ser. No. 62/037,650, filed Aug. 15, 2014, U.S. Provisional Application Ser. No. 62/037,652, filed Aug. 15, 2014, and U.S. Provisional Application Ser. No. 62/037,661, filed Aug. 15, 2014, the disclosures of which are hereby incorporated by reference herein in their entirety.

FIELD OF THE INVENTION

This invention relates to methods, systems, and computer program products, particularly to methods, systems, and computer program products for detecting pipette tip integrity.

BACKGROUND

The isolation of individual colonies of micro-organisms, particularly bacteria, is an important procedure in microbiological laboratories. Traditionally, the isolation of bacteria has been performed manually by skilled laboratory technicians who first dispense a microbiological sample onto the surface of a solid growth culture medium, such as agar in a Petri dish, followed by the use of a hand-tool to spread the sample across the surface of the medium, known as "streaking". However, these laboratory procedures can also be automated.

For both traditional, manual laboratory procedures and automated laboratory procedures, monitoring and/or verifying that a sample volume has been correctly dispensed onto a solid growth culture medium can be important. This is because if a sample has not been correctly dispensed, then it can create the risk of a false negative.

BRIEF SUMMARY

It is noted that aspects described with respect to one embodiment may be incorporated in different embodiments although not specifically described relative thereto. That is, all embodiments and/or features of any embodiments can be combined in any way and/or combination. Moreover, other systems, articles of manufacture, methods, and/or computer program products according to embodiments will be or become apparent to one with skill in the art upon review of the following drawings and detailed description. It is intended that all such additional systems, articles of manufacture, methods, and/or computer program products be included within this description, be within the scope of the present inventive concept, and be protected by the accompanying claims.

Some embodiments are directed to systems, articles of manufacture, methods and/or computer program products for detecting pipette tip integrity. In some embodiments, operations include collecting pressure data while aspirating a gas into a pipette tip attached to a pipette. In some embodiments, the pipette tip includes a filter. In some embodiments, the pressure data includes a plurality of pressure values measured at an internal portion of the pipette and taken over a given time interval. In some embodiments, the plurality of pressure values include a maximum pressure value and a minimum pressure value.

Some embodiments include estimating a pressure range value between the maximum pressure value and the minimum pressure value. In some embodiments, responsive to the pressure range value being greater than or equal to a lower threshold and the pressure range value being less than or equal to an upper threshold, it is determined that the pipette tip attached to the pipette is properly functioning. Some embodiments include, responsive to the pressure range value being less than a lower threshold. In some embodiments, responsive to the pressure range value being greater than an upper threshold, it is determined that the pipette tip attached to the pipette is not properly functioning.

In some embodiments, collecting pressure data while aspirating gas into the pipette tip attached to the pipette includes measuring pipette pressure at given time intervals. Some embodiments include aspirating gas into the pipette tip attached to the pipette over a given time interval.

In some embodiments, collecting pressure data while aspirating gas into the pipette tip attached to the pipette includes aspirating the gas at a given rate of aspiration. Some embodiments include aspirating gas a rate of aspiration in a range of about 300 µL/s to about 700 µL/s.

In some embodiments, collecting pressure data while aspirating gas into the pipette tip attached to the pipette includes aspirating gas into the pipette tip prior to aspirating a liquid into the pipette tip. Same embodiments include collecting pressure data while aspirating a given volume of gas into the pipette tip attached to the pipette.

In some embodiments, estimating the pressure range value between the maximum pressure value and the minimum pressure value includes subtracting the minimum pressure value from the maximum pressure value to obtain the pressure range value.

Some embodiments include that the upper threshold and/or the lower threshold is/are determined using a given rate of aspiration. In some embodiments, the given rate of aspiration is in a range of about 300 µL/sec to about 700 µL/sec. Some embodiments include that the given rate of aspiration is the same as the rate of aspiration for aspirating the gas into the pipette tip attached to the pipette.

Some embodiments include, responsive to the pressure range value being greater than or equal to the lower threshold and the pressure range value being less than or equal to the upper threshold, determining that the pipette tip attached to the pipette is suitable for use.

Some embodiments include, responsive to the pressure range value being greater than or equal to the lower threshold and the pressure range value being less than or equal to the upper threshold, aspirating a liquid into the pipette tip.

Some embodiments include, responsive to the pressure range value being less than the lower threshold or the pressure range value being greater than the upper threshold, removing the pipette tip from the pipette.

Some embodiments include, responsive to the pressure range value being less than the lower threshold or the pressure range value being greater than the upper threshold, determining that the pipette tip is defective, clogged, and/or improperly attached to the pipette.

Some embodiments include, detecting that the pipette tip is defective or without a filter responsive to the pressure range value being less than the lower threshold.

Some embodiments include, detecting that the pipette tip is defective responsive to the pressure range value being greater than the upper threshold. In some embodiments, the pipette tip is a clogged.

In some embodiments, the maximum pressure value is measured at a first point in time and the minimum pressure value is measured at a second point in time and the first point in time is before the second point in time. In some embodiments, the maximum pressure value is measured at a first point in time and the minimum pressure value is measured at a second point in time and the second point in time is before the first point in time.

Some embodiments are directed to systems, articles of manufacture, methods and/or computer program products for positioning a pipette and/or detecting a surface using a pipette. In some embodiments, operations include positioning a pipette at a first distance above a surface using a first position detector and positioning the pipette at a second distance above the surface using a second position detector that is different from the first position detector, wherein the second distance is less than the first distance. In some embodiments, the second position detector includes a pipette pressure detector and the first position detector uses a metric other than pressure. Some embodiments include, prior to positioning the pipette at the second distance, contacting the surface with a tip of the pipette.

In some embodiments, operations include measuring a pipette pressure at an internal portion of a pipette to generate a plurality of pipette pressure values. Some embodiments include determining a pressure difference relative to at least one previously measured pipette pressure value. Some embodiments include estimating at least one statistical variable corresponding to a rate of change in pipette pressure. In some embodiments, the at least one statistical variable is compared to at least one pipette pressure related threshold. Some embodiments include, responsive to comparing the at least one statistical variable to the at least one pipette pressure related threshold, estimating a pipette position. Some embodiments include, responsive to comparing the at least one statistical variable to the at least one pressure related threshold, determining if the surface has been contacted with the pipette tip.

In some embodiments, measuring the pipette pressure includes measuring the pipette pressure with a liquid and/or gas in a pipette tip attached to the pipette. In some embodiments, measuring the pipette pressure includes measuring the pipette pressure at given time intervals. Some embodiments include measuring the pipette pressure while aspirating gas into a pipette tip attached to the pipette and while the pipette is moving toward a surface and/or the surface is/are moving toward the pipette. In some embodiments, the pipette is moving downward in a z-direction toward the surface. Some embodiments include the pipette aspirating gas at a constant flow rate.

Some embodiments include, prior to estimating the at least one statistical variable, estimating the rate of change in pipette pressure. In some embodiments, estimating the rate of change in pipette pressure includes mathematically weighting the pressure difference to provide a weighted pressure difference. In some embodiments, estimating the rate of change in pipette pressure includes summing the weighted pressure difference with at least one weighted previously calculated rate of change in pipette pressure. In some embodiments, the pressure difference is weighted by about 0% to 49% and the previously calculated rate of change in pipette pressure is weighted by about 51% to about 100%.

In some embodiments, estimating the at least one statistical variable includes estimating an average rate of change in pipette pressure. In some embodiments, estimating the at least one statistical variable includes estimating a ratio relating to the rate of change in pipette pressure. In some embodiments, the ratio relating to the rate of change in pipette pressure includes the rate of change in pipette pressure and the average rate of change in pipette pressure.

In some embodiments, comparing the at least one statistical variable includes comparing the rate of change in pipette pressure to a first pressure related threshold and comparing a statistical variable to a second pressure related threshold. In some embodiments, the at least one pressure related threshold is determined using a given rate of aspiration and/or a given rate of movement. In some embodiments, the statistical variable is a ratio of the rate of change in pipette pressure divided by an average rate of change in pipette pressure. In some embodiments, the first pressure related threshold is a rate of change in pipette pressure threshold and the second pressure related threshold is a pipette pressure ratio threshold. Some embodiments include detecting contact with a surface detected when the rate of change in pipette pressure is less than or equal to the rate of change in pipette pressure threshold and the ratio of the rate change in pipette pressure divided by the average rate of change in pipette pressure is greater than or equal to the pipette pressure ratio threshold.

In some embodiments, estimating the pipette position includes estimating the position of a pipette tip relative to a surface. In some embodiments, estimating the pipette position includes determining that a surface is not in contact with the pipette and, responsive to determining that the surface is not in contact with the pipette, continuing to estimate the pipette position. In some embodiments, estimating the pipette position includes determining that a surface is in contact with the pipette. In some embodiments, determining if the surface has been contacted with the pipette tip includes estimating the position of the pipette tip relative to the surface.

Some embodiments include determining that the surface is in contact with the pipette by determining that the distal orifice of a pipette tip attached to the pipette has sealed with the surface. In some embodiments, determining that the surface is in contact with the pipette includes detecting at least two consecutive data points that indicate contact to the surface with the pipette.

Some embodiments include, responsive to determining that the surface is in contact with the pipette, stopping movement of the pipette toward the surface and adjusting the pipette to a position above the surface. In some embodiments, responsive to determining that the surface is in contact with the pipette, stopping movement of the surface toward the pipette and adjusting the surface to a position below the pipette. Some embodiments include, responsive to determining that the surface is in contact with the pipette, stopping the aspiration of gas.

In some embodiments, operations include aspirating a liquid into the pipette tip and positioning the pipette tip at a first distance above a surface. Some embodiments include moving the pipette toward the surface while aspirating gas into the pipette tip. Some embodiments include measuring pipette pressure at an internal portion of the pipette and collecting pipette pressure data. In some embodiments, measuring pipette pressure at an internal portion of the pipette includes generating a plurality of pipette pressure values. In some embodiments, the pipette pressure data includes the plurality of pipette pressure values. In some embodiments, contact to the surface with the pipette tip is detected using the pipette pressure data.

Some embodiments are directed to systems, articles of manufacture, methods and/or computer program products for verifying dispensing of a fluid from a pipette. In some embodiments, operations include collecting pressure data while dispensing fluid from a pipette tip attached to a pipette. In some embodiments, the pressure data includes a plurality of pressure values measured at an internal portion of the pipette and taken over a given time interval. In some embodiments, the plurality of pressure values includes a maximum pressure value and a minimum pressure value. Some embodiments include estimating a pressure range value between the maximum pressure value and the minimum pressure value. Some embodiments include determining that the fluid included a liquid, responsive to the pressure range value being greater than or equal to at least one threshold. Some embodiments include determining that the fluid did not include a liquid, responsive to the pressure range value being less than the at least one threshold.

In some embodiments, collecting pressure data while dispensing fluid from the pipette tip attached to the pipette includes measuring pipette pressure at given sampling time intervals. Some embodiments include dispensing fluid from the pipette tip attached to the pipette over the given time interval.

In some embodiments, collecting pressure data while dispensing fluid from the pipette tip attached to the pipette includes dispensing the fluid at a given rate. In some embodiments, the given rate is in a range of about 5 μL/sec to about 400 μL/sec.

Some embodiments include, prior to collecting pressure data while dispensing fluid from the pipette tip attached to the pipette, aspirating a gas into the pipette tip and subsequently aspirating a liquid into the pipette tip. In some embodiments, prior to collecting pressure data while dispensing fluid from the pipette tip attached to the pipette, at least a portion of the liquid is dispensed from the pipette tip.

In some embodiments, collecting pressure data while dispensing fluid from the pipette tip attached to the pipette includes dispensing all fluid present in the pipette tip in the given time interval.

In some embodiments, estimating the pressure range value between the maximum pressure value and the minimum pressure value includes subtracting the minimum pressure value from the maximum pressure value to obtain the pressure range value.

Some embodiments include prior to estimating the pressure range value between the maximum pressure value and the minimum pressure value, removing a portion of pressure values from the plurality of pressure values. In some embodiments, the portion of pressure values are a given number of consecutive pressure values. In some embodiments, the portion of pressure values includes the initial pressure value in the plurality of pressure values.

In some embodiments, determining that the fluid did not include a liquid indicates that a dispensing error occurred.

Some embodiments include estimating a pressure area ratio that identifies at least two pressure data curves, each of the at least two pressure data curves corresponding to at least a portion of the plurality of pressure values. In some embodiments, the pressure area ratio is compared to at least one threshold. Some embodiments include determining that the fluid included a sufficient amount of the liquid, responsive to the pressure area ratio being greater than at least one threshold. Some embodiments include determining that the fluid did not include a sufficient amount of the liquid, responsive to the pressure area ratio being less than or equal to at least one threshold.

In some embodiments, estimating the pressure area ratio includes estimating a maximum area corresponding to a pressure data curve that corresponds to the maximum pressure value and the minimum pressure value. In some embodiments, estimating the pressure area ratio includes estimating an actual pressure area corresponding to a pressure data curve that corresponds to the plurality of pressure values. Some embodiments include multiplying the pressure range value by the given time interval to estimate the maximum area. In some embodiments, the given time interval is the number of pressure values in the plurality of pressure values multiplied by the given sampling time interval between consecutive pressure values in the plurality of pressure values.

In some embodiments, estimating the actual pressure area includes summing areas of a plurality of rectangles. In some embodiments, a width of each rectangle of the plurality of rectangles is the given sampling time interval between consecutive pressure values in the plurality of pressure values. In some embodiments, a height of each rectangle of the plurality of rectangles is a midpoint between at least two consecutive pressure values minus the minimum pressure value.

In some embodiments, determining that the fluid did not include a sufficient amount of the liquid indicates that a dispensing error occurred.

Some embodiments are directed to systems, articles of manufacture, methods and/or computer program products for detecting a droplet. In some embodiments, operations include estimating a plurality of rate of change in pipette pressure values during a given time interval. Some embodiments include detecting the formation of a droplet at a distal end of a pipette tip attached to a pipette, responsive to at least one of the plurality of rate of change in pipette pressure values being greater than or equal to an upper pressure related threshold and at least one of the plurality of rate of change in pipette pressure values being less than or equal to a lower pressure related threshold.

In some embodiments, estimating the plurality of rate of change in pipette pressure values during the given time interval includes measuring a pipette pressure at an internal portion of a pipette at given sampling time intervals to generate a plurality of pipette pressure values. In some embodiments, estimating the plurality of rate of change in pipette pressure values during the given time interval includes determining a plurality of pressure differences relative to at least one previously measured pipette pressure value. In some embodiments, estimating the plurality of rate of change in pipette pressure values during the given time interval includes mathematically weighting each of the plurality of pressure differences to provide the plurality of rate of change in pipette pressure values.

In some embodiments, mathematically weighting each of the plurality of pressure differences to provide the plurality of rate of change in pipette pressure values includes weighting a most recently determined pressure difference to provide a weighted pressure difference. In some embodiments, mathematically weighting each of the plurality of pressure differences to provide the plurality of rate of change in pipette pressure values includes weighting at least one previously calculated rate of change in pipette pressure value to provide a weighted previously calculated rate of change in pipette pressure value. Some embodiments include summing the weighted pressure difference and the weighted previously calculated rate of change in pipette pressure value. In some embodiments, the most recently determined pressure difference is weighted by about 0% to 49% and the at least one previously calculated rate of change in pipette pressure value is weighted by about 51% to about 100%.

In some embodiments, the plurality of rate of change in pipette pressure values changes over a period of time.

Some embodiments include determining the upper pressure related threshold and/or the lower pressure related threshold using a given rate of dispense.

In some embodiments, the droplet has a volume in a range of about 0.5 µL to about 3.5 µL.

In some embodiments, at least one of the plurality of rate of change in pipette pressure values corresponds to a rate of change in pipette pressure while the pipette is dispensing a gas. In some embodiments, at least one of the plurality of rate of change in pipette pressure values corresponds to a rate of change in pipette pressure while the pipette is dispensing a liquid.

Some embodiments include, responsive to detecting the formation of the droplet, stopping dispensing of liquid from the pipette tip.

In some embodiments, a clog is detected in the pipette tip attached to the pipette. In some embodiments, detecting the clog in the pipette tip attached to the pipette includes determining that a given number of rate of change in pipette pressure values of the plurality of rate of change in pipette pressure values are greater than or equal to a first clog related threshold. In some embodiments, detecting the clog in the pipette tip attached to the pipette includes determining that an updated pressure difference corresponding to a most recently measured pipette pressure value of the plurality of pipette pressure values is greater than a second clog related threshold.

In some embodiments, the given number of rate of change in pipette pressure values of the plurality of rate of change in pipette pressure values corresponds to a given period of time.

Some embodiments include estimating the updated pressure difference. In some embodiments, estimating the updated pressure difference includes selecting a minimum pipette pressure value from the plurality of pipette pressure values and subtracting the minimum pipette pressure value from the most recently measured pipette pressure value of the plurality of pipette pressure values.

In some embodiments, the second clog related threshold corresponds to a cumulative rise in pressure of a given value. Some embodiments include determining the first clog related threshold and/or the second clog related threshold using a given rate of dispense.

Some embodiments include detecting that the pipette tip does not contain a liquid. In some embodiments, detecting that the pipette tip does not contain the liquid includes estimating a plurality of changes in pressure over a given period of time. In some embodiments, detecting that the pipette tip does not contain the liquid further includes determining that a portion of the plurality of changes in pressure indicate no significant change in pressure. In some embodiments, the portion of the plurality of changes in pressure that indicates no significant change in pressure is at least 50%.

In some embodiments, estimating the plurality of changes in pressure over the given period of time includes measuring the pipette pressure at an initial point in time and estimating the plurality of changes in pressure at a given point in time after the initial point in time.

Some embodiments include measuring a pipette pressure at an internal portion of the pipette including a pipette tip attached thereto to generate a plurality of pipette pressure values. In some embodiments, a pressure difference relative to at least one previously measured pipette pressure value is determined. Some embodiments include providing a plurality of pressure difference values. In some embodiments, a portion of the plurality of pressure difference values is compared with an upper pressure related threshold and a lower pressure related threshold. Some embodiments include detecting the formation of a droplet, responsive to determining that at least one pressure difference value of the portion of the plurality of pressure difference values is greater than or equal to the upper pressure related threshold and that at least one pressure difference value of the portion of the plurality of pressure difference values is less than or equal to the lower pressure related threshold.

In some embodiments, comparing the portion of the plurality of pressure difference values with the upper pressure related threshold and the lower pressure related threshold includes comparing a portion of a plurality of rate of change in pipette pressure values with the upper pressure related threshold and the lower pressure related threshold.

Some embodiments include estimating a rate of change in pipette pressure and providing a plurality of rate of change in pipette pressure values. In some embodiments, estimating the rate of change in pipette pressure includes mathematically weighting the pressure difference to provide a weighted pressure difference. In some embodiments, estimating the rate of change in pipette pressure includes summing the weighted pressure difference with at least one weighted previously calculated rate of change in pipette pressure. In some embodiments, the pressure difference is weighted by about 0% to 49% and the previously calculated rate of change in pipette pressure is weighted by about 51% to about 100%.

Some embodiments include measuring the pipette pressure at given sampling time intervals. In some embodiments, measuring the pipette pressure includes measuring the pipette pressure while the pipette is positioned at a given position.

In some embodiments, comparing the portion of the plurality of pressure difference values with the upper pressure related threshold and the lower pressure related threshold includes comparing at least two pressure difference values.

In some embodiments, the plurality of pressure difference values changes over a period of time.

Some embodiments include determining the upper pressure related threshold and/or the lower pressure related threshold using a given rate of dispense.

In some embodiments, the droplet has a volume in a range of about 0.5 µL to about 3.5 µL.

In some embodiments, at least one pressure difference value of the portion of the plurality of pressure difference values corresponds to a pipette pressure while the pipette is dispensing a gas. In some embodiments, at least one pressure difference value of the portion of the plurality of pressure difference values corresponds to a pipette pressure while the pipette is dispensing a liquid.

Some embodiments include, responsive to detecting the formation of the droplet, stopping dispensing of liquid from the pipette tip.

Some embodiments include detecting a clog in the pipette tip attached to the pipette. In some embodiments, detecting the clog in the pipette tip attached to the pipette includes determining that a given number of rate of change in pipette pressure values of the plurality of rate of change in pipette pressure values are greater than or equal to a first clog related threshold. In some embodiments, detecting the clog in the pipette tip attached to the pipette includes determining that an updated pressure difference corresponding to a most recently measured pipette pressure value of the plurality of pipette pressure values is greater than a second clog related threshold.

In some embodiments, the given number of rate of change in pipette pressure values of the plurality of rate of change in pipette pressure values corresponds to a given period of time.

Some embodiments include estimating the updated pressure difference. In some embodiments, estimating the updated pressure difference includes selecting a minimum pipette pressure value from the plurality of pipette pressure values and subtracting the minimum pipette pressure value from the most recently measured pipette pressure value of the plurality of pipette pressure values.

In some embodiments, the second clog related threshold corresponds to a cumulative rise in pressure of a given value. In some embodiments, the first clog related threshold and/or the second clog related threshold is/are determined using a given rate of dispense.

Some embodiments include detecting that the pipette tip does not contain a liquid. In some embodiments, detecting that the pipette tip does not contain a liquid includes estimating a plurality of changes in pressure over a given period of time. In some embodiments, detecting that the pipette tip does not contain the liquid includes determining that a portion of the plurality of changes in pressure indicate no significant change in pressure. In some embodiments, the portion of the plurality of changes in pressure that indicates no significant change in pressure is at least 50%.

In some embodiments, estimating the plurality of changes in pressure over the given period of time includes measuring the pipette pressure at an initial point in time and estimating the plurality of changes in pressure at a given point in time after the initial point in time.

In some embodiments, determining the pressure difference relative to the at least one previously measured pipette pressure includes measuring the pipette pressure at an initial point in time and determining the pressure difference relative to the least one previously measured pipette pressure at a given point in time after the initial point in time. Some embodiments include that the given point in time after the initial point in time corresponds to a volume of gas present in the distal portion of the pipette tip at the initial point in time.

Some embodiments of the present disclosure are directed to computer program products that include a computer readable storage medium having computer readable program code embodied in the medium. The computer code may include computer readable code to perform any of the operations as described herein.

Some embodiments of the present disclosure are directed to a computer system that includes at least one processor and at least one memory coupled to the processor. The at least one memory may include computer readable program code embodied therein that, when executed by the at least one processor causes the at least one processor to perform any of the operations as described herein.

It is noted that aspects of the disclosure described with respect to one embodiment, may be incorporated in a different embodiment although not specifically described relative thereto. That is, all embodiments and/or features of any embodiment can be combined in any way and/or combination. These and other objects and/or aspects of the present inventive concept are explained in detail in the specification set forth below.

BRIEF DESCRIPTION OF THE DRAWINGS

Aspects of the present disclosure are illustrated by way of example and are not limited by the accompanying figures with like references indicating like elements.

DETAILED DESCRIPTION

As discussed herein, systems, articles of manufacture, methods, and/or computer program products of the present inventive subject matter may provide an effective and efficient way to detect pipette tip integrity. Some embodiments of the present inventive subject matter may provide the ability to monitor and/or verify that a liquid sample volume is correctly dispensed onto a surface of a target, such as a surface of solid growth culture medium (e.g., agar). Thus, some embodiments of the present inventive subject matter may reduce the risk of a false negative. For example, if a pipette tip is not functioning properly (e.g., there is a clog or leak in the pipette tip or the pipette tip is not installed or attached properly), then no or an insufficient amount of a liquid sample may be dispensed onto a surface, such as a surface of solid growth culture medium (e.g., agar). This may result in a false negative if the condition is not detected. Some embodiments of the present inventive subject matter may provide the ability to detect and/or determine the integrity of a pipette tip and/or if a pipette tip is functioning properly. In some embodiments, it may be determined if a pipette tip is suitable for use or is not suitable for use. In some embodiments, determining that a pipette tip is suitable for use includes determining that that a pipette tip attached to a pipette is suitable to aspirate and dispense a liquid. Some embodiments include, responsive to determining that a pipette tip is functioning properly and/or suitable for use, aspirating a liquid into the pipette tip. "Liquid" as used herein refers to a sample having a viscosity suitable for aspirating and dispensing using a pipette, but which may include solid particles. In some embodiments, the liquid sample is a biological sample.

In some embodiments, systems, articles of manufacture, methods, and/or computer program products of the present inventive subject matter may be used with and/or in an automated apparatus. The automated apparatus may be an apparatus for positioning a pipette and/or for pipetting a liquid onto a surface of a target, such a surface of solid growth culture medium (e.g., agar). In some embodiments, the automated apparatus may be an apparatus for inoculating and streaking a solid growth culture medium in a plate, such as, for example, the apparatus illustrated in FIGS. 1 and 2.

Figure 1:
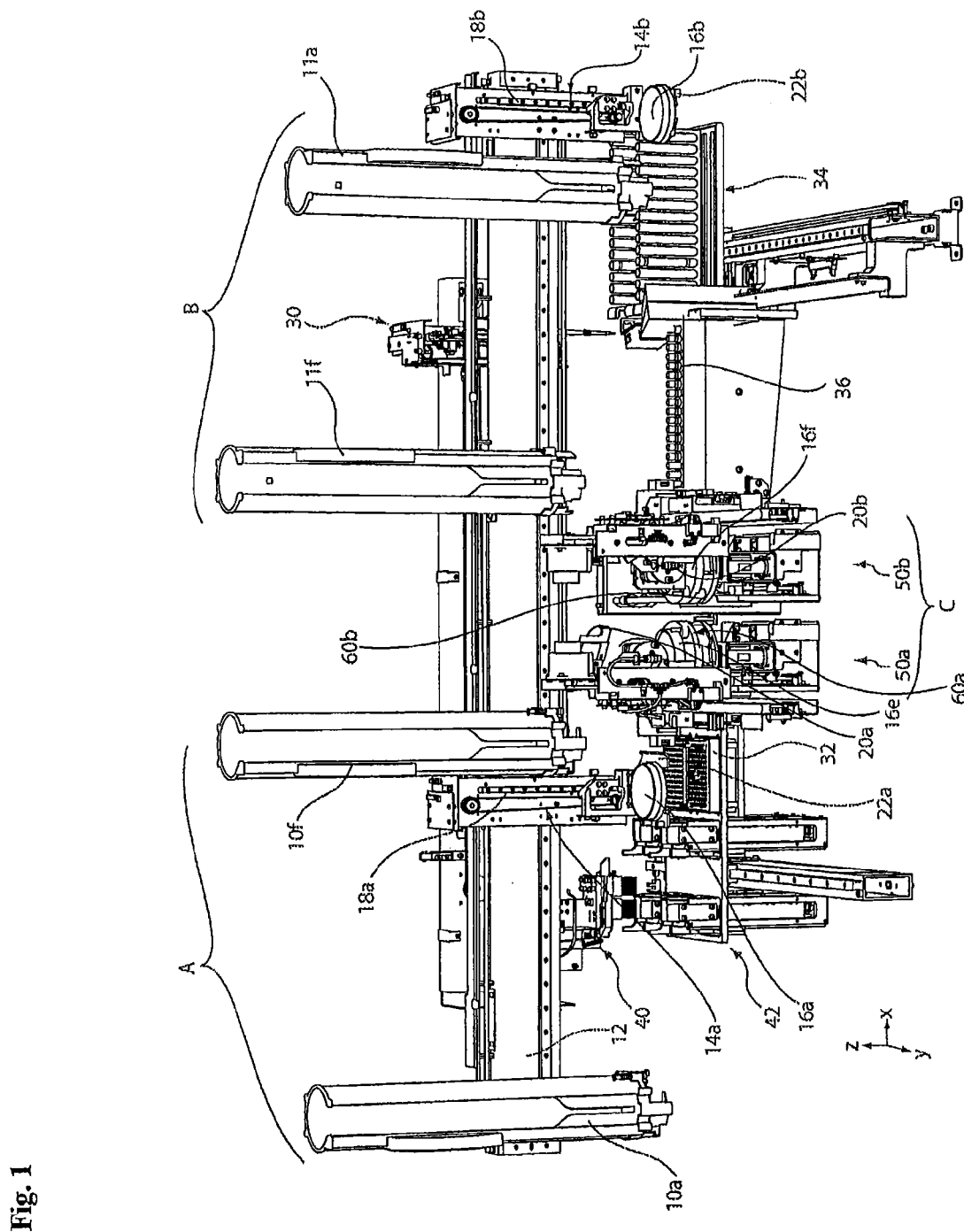
FIG. 1 is a perspective view from the front of an automated streaking apparatus according to some embodiments of the present inventive subject matter.
Figure 2:
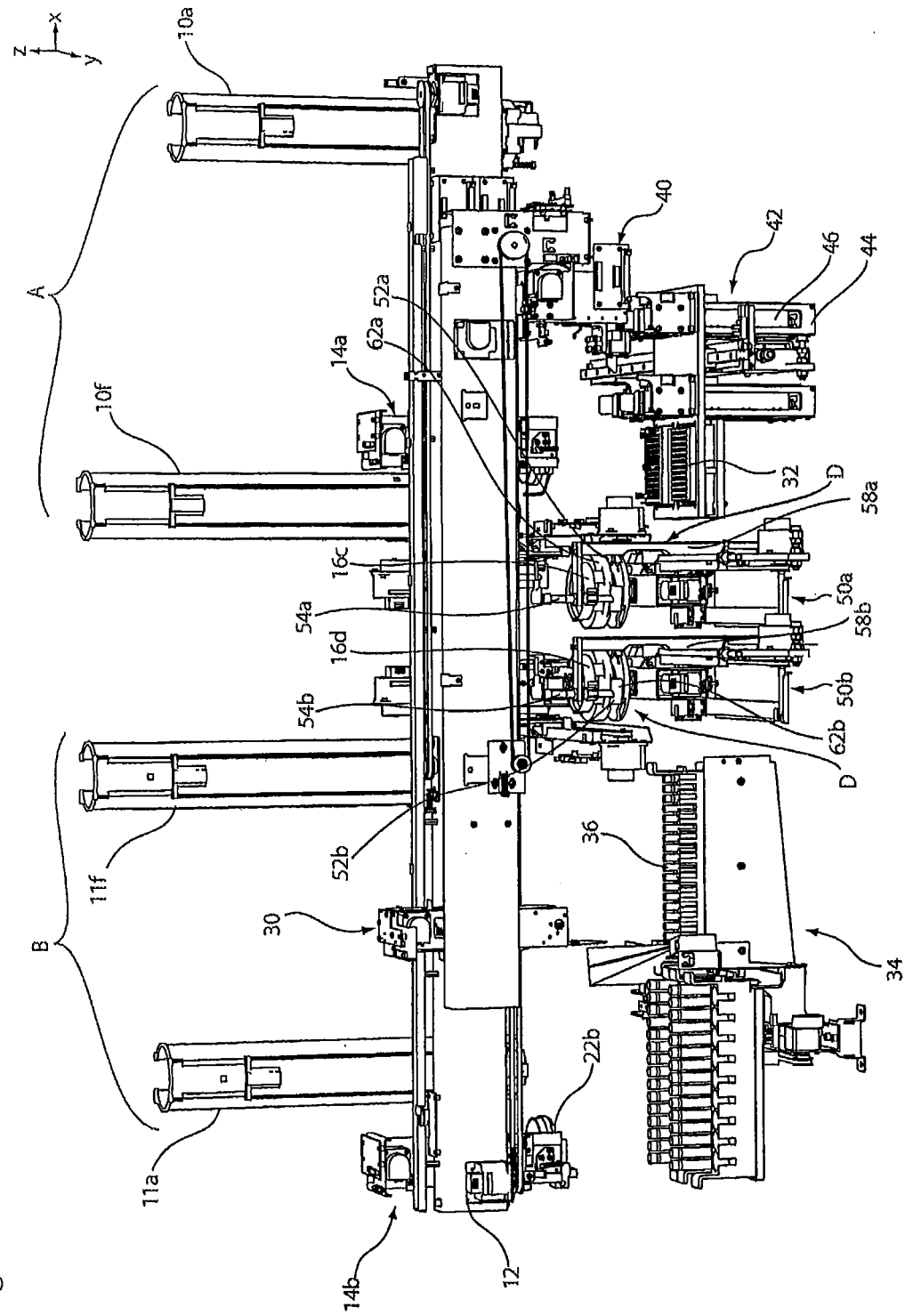
FIG. 2 is a perspective view from the rear of the apparatus of FIG. 1 according to some embodiments of the present inventive subject matter.

Reference is now made to FIGS. 1 and 2, which are a perspective view from the front and rear, respectively, of an automated streaking apparatus according to some embodiments of the present inventive subject matter. The apparatus includes a plate supply (indicated by the letter A) that includes a plurality of input plate cassettes 10 (only cassettes 10a and 10f are shown) supported on an upper frame (not shown) for the supply of raw plates to the apparatus, together with a plate store (indicated by the letter B) that includes a plurality of output plate cassettes 11 (only cassettes 11a and 11f are shown) also supported on the upper frame for the storage of processed plates from the apparatus. Also shown in FIG. 1 is an inoculation and streaking station (indicated by the letter C).

In some embodiments, the plate supply A and the plate store B are supported by the upper frame so as to be in front of a main gantry 12, along which various of operative carriages of the apparatus may move, as will be explained below. The various parts of the inoculation and streaking station C may be supported by a lower frame (not shown).

Operatively engaged for sliding movement along the main gantry 12 is a plate supply carriage 14a and a plate store carriage 14b, which form a part of a plate transfer feed mechanism and a plate transfer store mechanism, respectively. These carriages are both configured for movement along the main gantry 12 (in the x direction) to move a plate (16a or 16b) from the plate supply A to the inoculation and streaking station C and then to the plate store B. The carriages 14a, 14b are also configured to provide movement of a plate 16a, 16b along vertical guiderails 18a, 18b thereon to raise and/or lower such plate 16a, 16b in the z direction to or from the respective cassettes 10a to 10f, and 11a to 11f and to or from either or both of the dual plate orientation mechanisms 20a, 20b.

In this respect, it can be seen that each of the carriages 14a, 14b includes a plate support tray 22a, 22b upon which the plates 16a, 16b rest in transit, the plate support trays 22a, 22b being suitably mounted to their respective carriages for the movement described above. In some embodiments, the plates 16a, 16b may be supplied and stored in their respective cassettes 10a-10f, 11a-11f in an inverted orientation, such that their bottoms are uppermost and their lids are lowermost.

Also configured for movement along the main gantry 12 are an inoculating device 30 and a streaking device 40. In some embodiments, both may be mounted upon a suitable carriage for movement along the main gantry in the x direction. The inoculation device 30 may include a pipette robot system controlled so as to be able to access supply 32 of pipette tips and a sample supply system 34 that includes a number of supply tubes 36, and to access a plate work position (one such position shown in FIG. 2 by the letter D) for inoculation purposes. The streaking device 40 may include a streaking robot system controlled so as to be able to access a streaking applicator supply 42 that, in some embodiments, includes four applicator supply cartridges 46 received in four corresponding cartridge holders 44.

In some embodiments, the inoculation and streaking station C of the apparatus includes dual plate work positions D and dual rotation devices 52a, 52b for the streaking of dual plates 16c, 16d as shown in FIG. 2 in the dual plate work positions D, and dual plate orientation mechanisms 20a, 20b, the location of which is indicated in FIGS. 1 and 2 by the reference numerals 50a and 50b. While FIG. 2 generally shows de-lidded plates 16c, 16d in the plate work positions D underneath dual sensors 54a, 54b, FIG. 1 shows dual plates 16e, 16f being orientated and de-lidded by the dual orientation mechanisms 20a, 20b. It will of course be appreciated that such a dual configuration is not essential for an apparatus in accordance with the present invention, and that single such stations and devices could be used. Indeed, an apparatus that includes three or four or more such stations and devices is also envisaged.

In some embodiments, the inoculating and streaking station C is the general location within the apparatus where the main functions of the apparatus occur, which location is generally centered around the plate work positions D. In some embodiments, the plate work positions D are defined by the physical location in the apparatus of the sensors 54a, 54b, which may be rigidly mounted to respective sensor mounting frames 58a, 58b. The apparatus may also include dual plate platforms for supporting a plate, although the combination of FIGS. 1 and 2 shows four such platforms, being the dual platforms 60a, 60b in the positions shown in FIG. 1, and the platforms 62a, 62b shown in FIG. 2. In this respect, these figures each show two platforms (in different positions) simply for the sake of description.

In some embodiments, each cassette 10a, 11a may be able to hold multiple plates within their inner chambers. For example, cassette 10a may hold multiple plates for the purpose of providing raw plates to the apparatus for subsequent processing, and cassette 11a may hold multiple plates for the purpose of storing processed plates following inoculation and streaking in the apparatus. As can be seen in FIGS. 1 and 2, each of the cassettes 10a, 11a also interacts with its respective carriage 14a, 14b to capture a plate, from below, on the respective trays 22a, 22b due to respective internal engaging and plate release/lock means (not shown).

In some embodiments, the inoculating device 30 of the apparatus of the present invention may be any device that is able to obtain and hold a sample, generally in a liquid form, and transfer that sample to a surface, such as the surface of a medium in a positioned plate. In some embodiments, the inoculating device 30 may be a pipette 31 mounted to a robot system (not shown) so as to be movable in the z-direction, as well as the x- and y-directions along the main gantry 12 as mentioned above. In some embodiments, the pipette 31 may include a pressure transducer configured to monitor pressure and/or vacuum profiles in an internal portion of the pipette 31.

Figure 3:
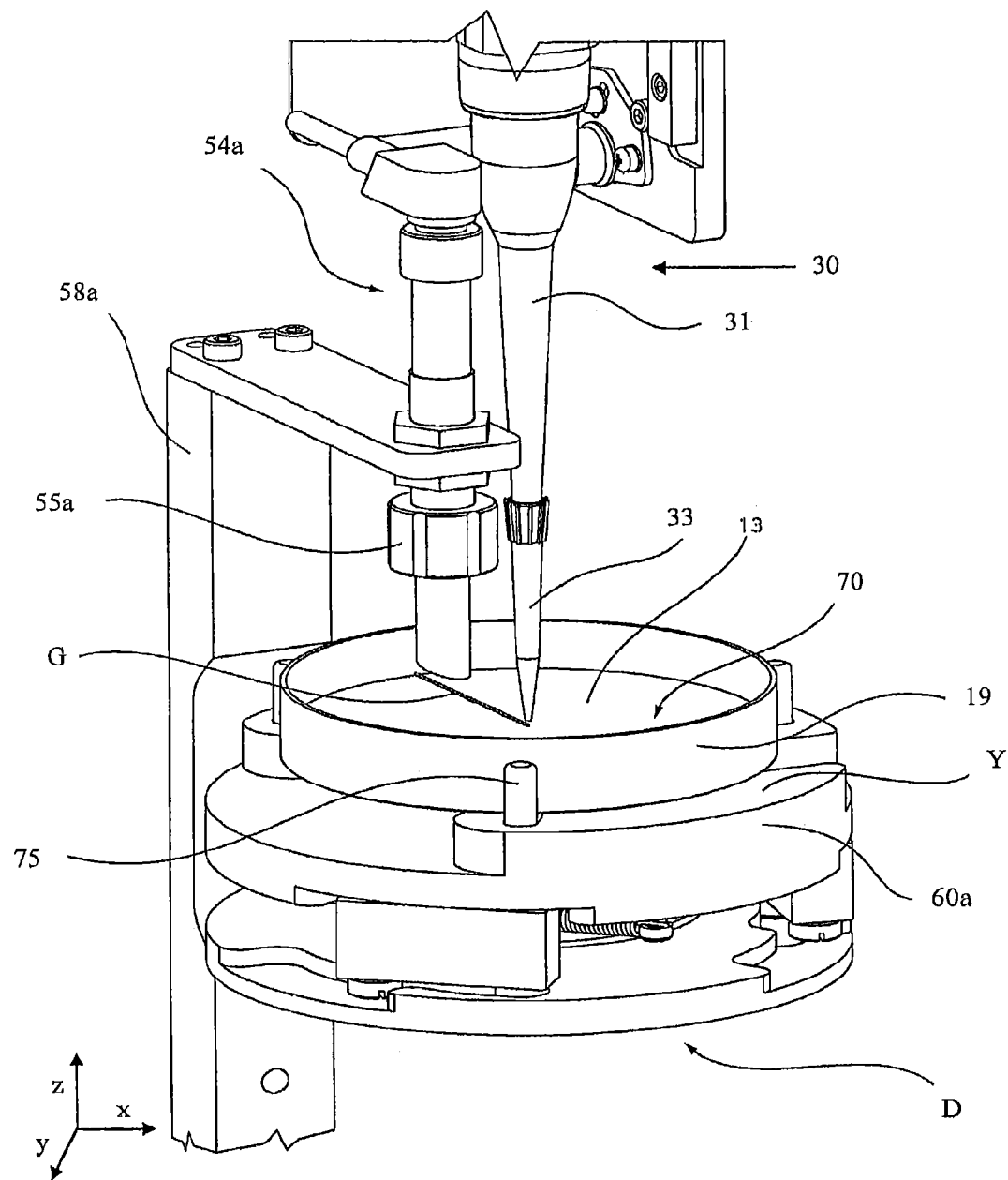
FIG. 3 is a perspective view from above a part of the apparatus of FIG. 1 according to some embodiments of the present inventive subject matter.

Reference is now made to FIG. 3, which is a perspective view from above a part of the apparatus of FIG. 1 according to some embodiments of the present inventive subject matter. The pipette 31 may include a pipette tip 33 releasably secured thereto. In some embodiments, the pipette tip 33 may include a filter and/or may be disposable. The pipette tip 33 may be releasably secured and/or attached to the pipette 31 in a manner that permits easy disposal of the pipette tip 33, such as disposal after inoculation has been affected. In some embodiments, the pipette 31 may be programmable for aspirating and/or dispensing various sample volumes at given points in time. In some embodiments, the pipette 31 may include a positional height referencing system, such as, but not limited to, a positional height z-direction referencing system. The positional height referencing system may be configured to determine in three dimensional space the height location of the pipette tip 33 relative to the datum level and reference points of a platform, such as platform

60*a*, 60*b*, 62*a*, 62*b*, as will be described below, and/or relative to a notional action line.

In some embodiments, the pipette robot system may be configured to move the pipette 31 to access a pipette tip supply 32, which may include a rack of pipette tips 33, to access the biological sample station 34, which may include a rack of sample containers such as sample tubes, to access the plate work position D in the inoculating and streaking station C, and/or to access a tip waste disposal area or chute. The pipette robot system, pipette 31, and/or pipette tip 33 may include suitable tip securing means that is configured for the pipette tip 33 to be secured to the pipette 31. In some embodiments, the pipette robot system, pipette 31, and/or pipette tip 33 may be configured to obtain and hold a sample, to dispense sample, and to dispose of a used pipette tip 33.

Referring again to FIG. 3, FIG. 3 illustrates some of the structures used for operations that may occur in the plate work position D and illustrates a plate platform 60*a* with a plate bottom 19 in a centralized and clamped position in the plate work position D. In some embodiments, the plate platform 60*a* may include a plate clamping member 75 in the form of three movable lugs operated by a camming device (not shown), which lugs may be configured to function as a plate centralizing means for centralizing the position of the plate bottom 19 on the platform 60*a*.

In some embodiments, the plate work position D may include a notional action line fixed in two dimensions (x,y) in a given position, together with a datum level Y (e.g., the surface upon the plate platform 60*a*). The action line is herein referred to as being a "notional" action line given that it will not be a visible action line and also will not have a determined position in three dimensional space until the height of the surface 70 of the medium in the plate bottom 19 is determined.

In some embodiments, the plate work position D may include a position detector, such as, for example, 1, 2, 3, 4, or more position detectors. The position detector may be configured and/or used to locate the surface 70 in a plate bottom 19 and/or to detect the z-position of medium in the plate bottom 19. In some embodiments, the position detector may include a sensor 54*a*. In some embodiments, the plate work position D may include a datum level Y, which may be the uppermost surface upon the plate platform 60*a*. In some embodiments, the sensor 54*a* may include an ultrasonic sensing device 55*a* having an ultrasonic beam focusing element that is configured to provide a focused beam on the surface 70 and/or within a sensing region that is central to the notional action line. The sensor 54*a* may be rigidly mounted via a sensor support arm 58*a*, thereby defining the general location of the plate work position D. In some embodiments, the sensor 54*a* may be mounted so that it is above the plate work position D and is operatively adjacent the plate bottom 19 held immediately therebelow in the plate platform 60*a*, the plate bottom 19 having its surface 70 open upwardly. In some embodiments, the sensor 54*a* may be positioned over a plate bottom 19, but may not be positioned over the starting position for dispensing a sample from a pipette tip 33.

In some embodiments, the sensor 54*a* may be configured to sense the surface 70 and/or measure the distance to the surface 70. The measured distance may then be referenced to the datum level Y to determine a surface positional reference relative to the datum level Y in one dimension (z) for the surface 70 in the plate bottom 19. In this manner, it will be appreciated that the surface 70 can thus be located in at least the z dimension by virtue of the determination of this surface positional reference. This may effectively determine the height of the medium in the plate bottom 19, at least with reference to that datum level Y. In this respect, and as can be seen in the figures, the datum level Y is a surface that forms a part of the plate platform 60*a* upon which the plate is clamped and supported. Therefore, in some embodiments, the determination of the surface positional reference effectively determines the height of the medium with reference to the plate platform 60*a* upon which it rests.

In some embodiments, the surface positional reference may be used together with the notional action line to determine the line G in three dimensions (x,y,z) that is representative of a line across the surface 70 in the positioned plate.

In some embodiments, the notional three dimensional action line that is represented by the line G across the surface 70 of the medium in the plate bottom 19 will be specific to the medium in that plate bottom 19 only, and may be a different three dimensional action line compared to the surface of the next plate processed in the plate work position D. In some embodiments, the given (x, y) position of the notional action line is, with reference to the circular plate bottom 19, located such that the notional action line will be a radial line for a circular plate. In some embodiments, this means that the line G, which represents the action line in three dimensions (x, y, z), will also be a radial line.

In some embodiments, once the position of the three dimensional action line G for a medium in a given positioned plate in three dimensional space has been determined, the sample may be deposited onto the surface 70 of the medium along the line G. As used herein, the reference to a sample being dispensed "along" a line or there being inoculation "along" a line, is intended to include a variety of forms of dispensing/inoculation. For example, a sample may be dispensed continuously along the full length of the line, or may be dispensed semi-continuously along the line, such as may be provided by a series of discrete deposits in the form of dots and/or dashes. Similarly, some embodiments include that a sample may be dispensed in a substantially non-linear form.

In some embodiments, the position detector may include a camera. The camera may be configured and/or used to detect the z-position of a pipette tip 33. In some embodiments, the camera and/or sensor 54*a* may be used to determine the three dimensional action line G for a medium.

In some embodiments, a pipette pressure detector may be used to determine the surface of medium in a positioned plate. Some embodiments include using a pipette pressure detector to determine the surface of medium in a positioned plate after and/or during a camera and/or sensor 54*a* determining the three dimensional action line G for the medium. In some embodiments, the pipette pressure detector may more accurately determine the surface of the medium than the camera and/or sensor 54*a*.

In some embodiments, a pipette pressure detector may be used to detect and/or determine the integrity of the pipette tip 33 attached to the pipette 31. Some embodiments include using the pipette pressure detector to detect and/or determine that the pipette tip 33 is functioning properly and/or is suitable for use. In some embodiments, determining that the pipette tip 33 is suitable for use includes determining that the pipette tip 33 attached to pipette 31 is suitable to aspirate and dispense a liquid. Some embodiments include using the pipette pressure detector to detect and/or determine that the pipette tip 33 is not functioning properly and/or is not suitable for use. In some embodiments, the pipette pressure detector may be used to detect and/or determine the integrity of the pipette tip 33 prior to aspirating a liquid sample into the pipette tip 33 and/or prior to determining the surface of medium in a positioned plate.

In some embodiments, a pipette pressure detector may be used to determine and/or verify dispensing of a fluid from the pipette tip 33 attached to the pipette 31. Some embodiments include detecting that a liquid is/was present in pipette tip 33 after a given amount of the liquid has been dispensed from the pipette tip 33 using a pipette pressure detector. Some embodiments include determining that a sufficient amount of liquid is/was present in the pipette tip 33 after a given amount of the liquid was dispensed from the pipette tip 33 using a pipette pressure detector. Some embodiments include determining and/or verifying dispensing of a fluid from the pipette tip 33 attached to the pipette 31 after the pipette pressure detector has determined and/or detected the surface of medium in a positioned plate. In some embodiments, the fluid is a liquid.

In some embodiments, a pipette pressure detector may be used to detect a droplet at the distal end of pipette tip 33 attached to the pipette 31 and/or the formation of a droplet at the distal end of pipette tip 33 attached to the pipette 31. Some embodiments include using the pipette pressure detector to detect a droplet and/or the formation of a droplet at the distal end of pipette tip 33 after the pipette pressure detector has determined the surface of medium in a positioned plate and/or after the pipette 31 has been positioned at a location for dispensing a liquid sample.

In some embodiments, a pipette pressure detector may be used to detect a clog in the pipette tip. In some embodiments, a pipette pressure detector may be used to detect an empty pipette tip (i.e., a pipette tip with no liquid present in the pipette tip).

The pipette pressure detector may include a pressure transducer and a pressure data module. In some embodiments, the pressure transducer and pressure data module may be integrated into a single package. In some embodiments, the pipette pressure detector may be mounted onto the pipette 31 and/or may be integral to the pipette 31. The pressure transducer may be in fluidic communication with an internal portion of the pipette 31 and/or may be built-in to the pipette 31. The pressure data module may receive and/or transmit signals corresponding to a pressure at an internal portion of the pipette 31. Some embodiments include the pressure data module receiving signals from the pressure transducer. In some embodiments, the pressure data module may convert a signal received from the pressure transducer to a different signal and/or signal format, such as, for example, from an analog signal to a digital signal. In some embodiments, the pipette pressure detector may be used to calculate the z-position relative to the surface 70 to move the pipette tip 33 to a desired position before the sample is dispensed from the pipette tip 33.

Some embodiments include using a pipette pressure detector to detect that the surface of a medium in a given plate is at a desired position for dispensing a sample from the pipette tip 33. In some embodiments, the desired position may be over the starting position for dispensing the sample from the pipette tip 33. Some embodiments include dispensing a liquid sample from the pipette tip 33 after a pipette pressure detector has determined the position of the surface of a medium in a given plate relative to the pipette tip 33 and/or after the pipette 31 has been moved to a z-position above the surface.

In some embodiments, while the liquid sample is being dispensed from the pipette tip 33, a pipette pressure detector may detect a droplet and/or the formation of a droplet at the distal end of pipette tip 33 attached to pipette 31. Some embodiments include stopping dispensing of the liquid sample from pipette tip 33 upon detecting the droplet and/or the formation of the droplet at the distal end of pipette tip 33 attached to pipette 31. In some embodiments, after detecting the droplet and/or the formation of the droplet at the distal end of pipette tip 33, the pipette 31 may be moved to a different position, such as, for example, a different position above the surface, and/or a second droplet may be detected at the distal end of pipette tip 33 attached to pipette 31.

In some embodiments, upon dispensing a liquid sample from the pipette tip 33 onto the surface 70 of the medium, a pipette pressure detector may be used to determine and/or verify that a remaining volume and/or a sufficient amount of the liquid sample is/was present in the pipette tip 33. In some embodiments, upon dispensing a liquid sample from the pipette tip 33 onto the surface 70 of the medium, the dispensed liquid may be streaked using the streaking device 40. In some embodiments, a line of spaced apart contact surfaces of a streaking applicator may contact at least a portion of the dispensed liquid, optionally along line G, on the surface 70 of the medium in the plate bottom 19. In some embodiments, the streaking applicator may contact the dispensed liquid and/or medium with a given contact pressure. In some embodiments, the given contact pressure may be suitable for the particular streaking applicator being used, for the composition of the liquid sample, and/or for the particular solid growth medium being used. In some embodiments, the given contact pressure may be such that the liquid is spread when the platform 60a is rotated and such that the streaking applicator does not undesirably gouge the surface of the medium.

As those of skill in the art will understand and appreciate, the above apparatus described in reference to FIGS. 1-3 is described only to provide an example embodiment in which systems, articles of manufacture, methods, and/or computer program products of the present inventive subject matter may be embodied. The above discussion is not intended to limit the systems, articles of manufacture, methods, and/or computer program products of the present inventive subject matter to the above-referenced apparatus. Instead, the apparatus described above in reference to FIGS. 1-3 is a non-limiting example and the systems, articles of manufacture, methods, and/or computer program products of the present inventive subject matter may be applied to any system, article of manufacture, method, and/or computer program product in which pipette controls may be utilized, in which detecting a surface relative to a pipette may be desired, and/or in which determining a pipette position relative to a surface may be desired.

Figure 4:
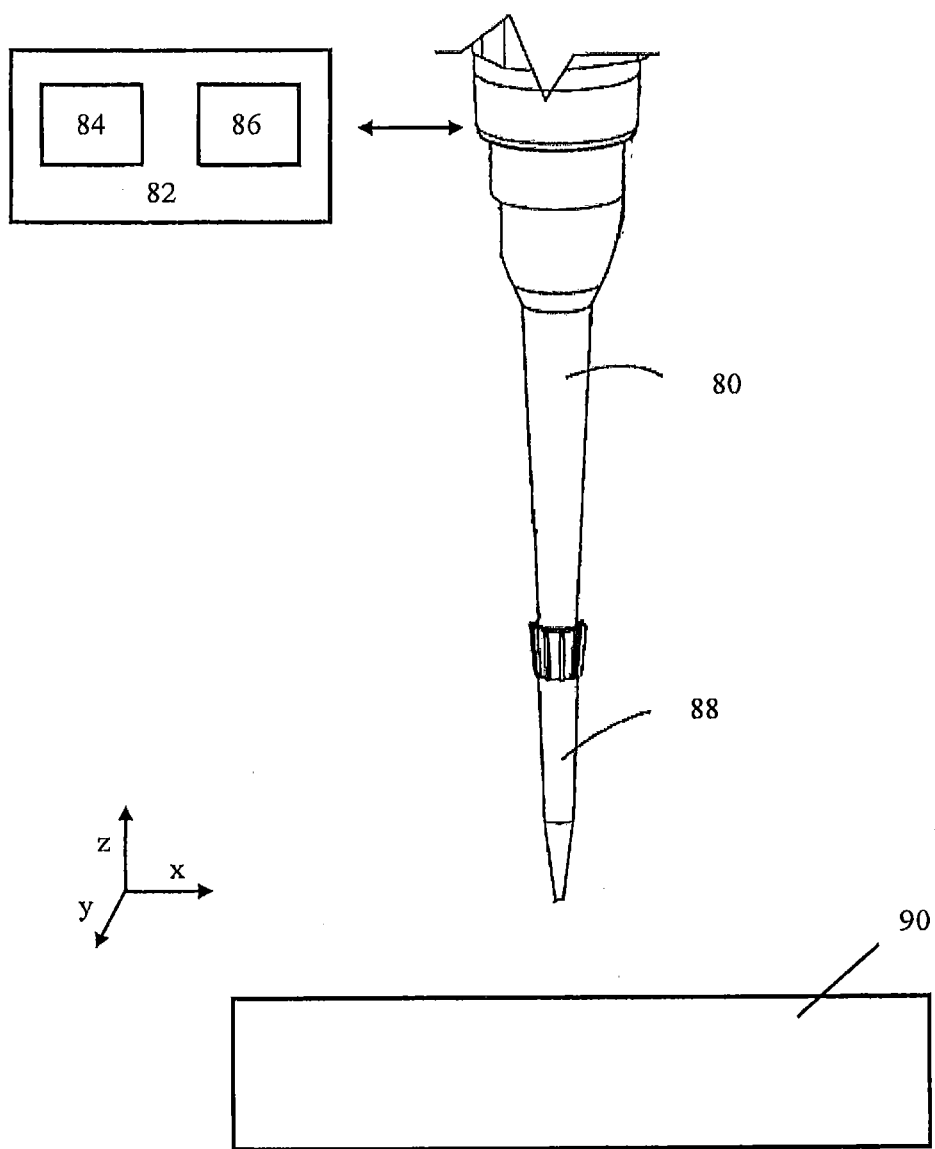
FIG. 4 is a perspective view of a pipette pressure detector according to some embodiments of the present inventive subject matter.

Reference is now made to FIG. 4, which is a perspective view of a pipette 80 according to some embodiments of the present inventive subject matter. In some embodiments, the pipette 80 may include a pipette tip 88 releasably attached to the pipette 80. In some embodiments, systems, articles of manufacture, methods, and/or computer program products of the present inventive subject matter may include a pipette pressure detector 82. The pipette pressure detector 82 may include a pressure transducer 84 and a pressure data module 86. In some embodiments, the pressure transducer 84 and pressure data module 86 may be integrated into a single package. In some embodiments, the pipette pressure detector 82 may be mounted onto the pipette 80 and/or may be integral to the pipette 80.

The pressure transducer 84 may be in fluidic communication with the pipette 80 and/or may be built-in to the pipette 80. The pressure data module 86 may receive and/or transmit signals corresponding to a pressure at an internal portion of the pipette 80. Some embodiments include the pressure data module 86 receiving signals from the pressure transducer 84. In some embodiments, the pressure data module 86 may convert a signal received from the pressure transducer 84 to a different signal and/or signal format, such as, for example, from an analog signal to a digital signal.

The pipette pressure detector 82 may measure pressure and/or vacuum profiles at an internal portion of a pipette. Example pipette pressure detectors that include a pipette include, but are not limited to, those commercially available from Tecan under the name CAVRO® and from Hamilton Company under the name ZEUS™. In some embodiments, the pipette pressure detector 82 may use pressure data to detect and/or determine the integrity of the pipette tip 88. In some embodiments, the pipette pressure detector 82 may use pressure data to determine that the pipette tip 88 is properly functioning and/or is suitable for use. In some embodiments, determining that the pipette tip 88 is suitable for use includes determining that that the pipette tip 88 attached to pipette 80 is suitable to aspirate and dispense a liquid. Some embodiments include using the pipette pressure detector to detect and/or determine that the pipette tip 88 is not functioning properly and/or is not suitable for use. Some embodiments include aspirating a gas into the pipette tip 88 while the pipette pressure detector 82 may be measuring pressure and/or vacuum profiles at an internal portion of the pipette 80 to determine whether the pipette tip 88 attached to pipette 80 is properly functioning and/or suitable for use.

In some embodiments, the pipette pressure detector 82 may use real-time pressure data to detect a surface 90 and/or to determine a position of the pipette 80 and/or pipette tip 88 above a surface 90.

In some embodiments, the pipette pressure detector 82 may use pressure data to determine and/or verify dispensing of a fluid in the pipette tip 88 attached to the pipette 80. In some embodiments, the fluid is a liquid. Some embodiments include determining and/or verifying dispensing of a fluid from the pipette tip 88 attached to the pipette 80 after a given volume of fluid has been dispensed. In some embodiments, the pipette pressure detector may be used to determine and/or verify that a sufficient volume of liquid is/was present in the pipette tip 88 after a portion of the liquid was dispensed.

In some embodiments, the pipette pressure detector 82 may use real-time pressure data to detect a droplet at the distal end of pipette tip 88 attached to pipette 80 and/or the formation of a droplet at the distal end of pipette tip 88 attached to a pipette 80. In some embodiments, the pipette pressure detector 82 may be used to detect a clog in the pipette tip 88. In some embodiments, the pipette pressure detector 82 may be used to detect an empty pipette tip (i.e., a pipette tip with no liquid present in the pipette tip).

The pipette pressure detector 82 may perform and/or be utilized in one or more operations of the methods and systems described below.

Figure 5:
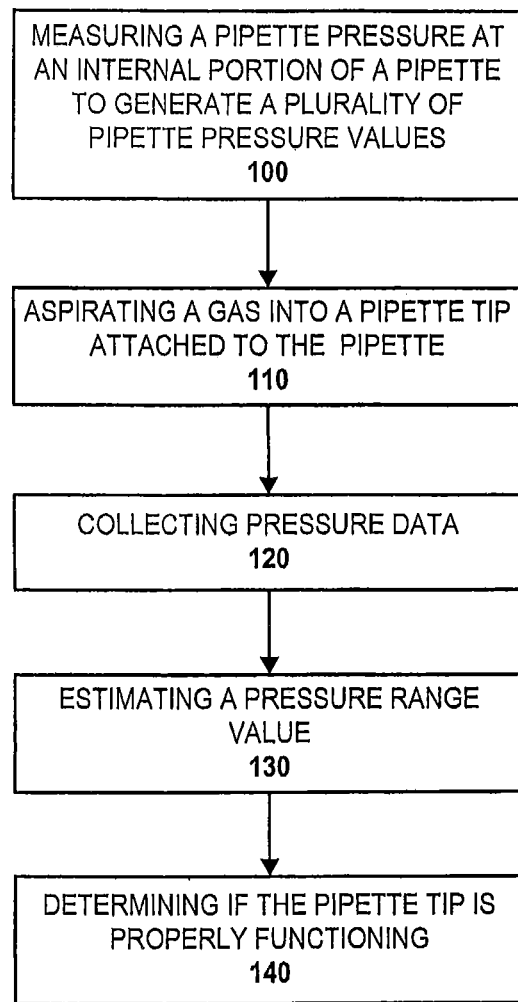
FIG. 5 is a flowchart illustrating operations in methods according to some embodiments of the present inventive subject matter.

Reference is now made to FIG. 5, which is a flowchart illustrating operations of methods according to some embodiments of the present inventive subject matter. The methods may include measuring a pipette pressure at an internal portion of a pipette at block 100. In some embodiments, measuring a pipette pressure at an internal portion of a pipette at block 100 may include generating a plurality of pipette pressure values. In some embodiments, measuring the pipette pressure at an internal portion of the pipette at block 100 is carried out using a pipette pressure detector including a pipette as described above in reference to FIG. 4. The duplicate discussion of the pipette pressure detector and pipette is omitted herein for the purposes of discussing FIG. 5.

Some embodiments include measuring pipette pressure at block 100 at given sampling time intervals and/or over a given time interval. Any suitable time interval may be used to measure the pipette pressure at block 100. In some embodiments, the total time interval over which pipette pressure is measured at block 100 may depend on the volume of a gas aspirated into a pipette tip attached to a pipette. In some embodiments, the total time interval over which pipette pressure is measured at block 100 may depend on the rate of aspiration of a gas into a pipette tip attached to a pipette.

Some embodiments include measuring pipette pressure at block 100 at sampling time intervals of every 0.1 to 100 milliseconds, such as, for example, every 1 to 50, 0.1 to 10, 1 to 10, 10 to 50, or 50 to 100 milliseconds. In some embodiments, pipette pressure at block 100 is measured at sampling time intervals of every 0.5, 1, 2, 3, 4, 5, 6, 7, 8, 9, 10, 20, 30, 40, or more milliseconds. Thus, the total time interval over which pipette pressure is measured at block 100 may be the sum of each sampling time interval. The given time intervals provided herein are examples and are not intended to limit the scope of the invention. For example, the pipette pressure may be measured at sampling time intervals less than 0.1 milliseconds or greater than 100 milliseconds.

Some embodiments include aspirating a gas into a pipette tip attached to a pipette at block 110. In some embodiments, the pipette tip includes a filter. In some embodiments, measuring a pipette pressure at an internal portion of a pipette at block 100 may include measuring pipette pressure while aspirating a gas into the pipette tip attached to the pipette at block 110.

In some embodiments, gas may be aspirated into the pipette tip at block 110 at a known flow rate; however, the gas may be aspirated into the pipette tip at any suitable flow rate. In some embodiments, the flow rate may depend on the characteristics of the pipette tip. Some embodiments may include tuning the flow rate based on the characteristics of the pipette tip. In some embodiments, gas may be aspirated into the pipette tip at a constant flow rate. Some embodiments include aspirating a gas into a pipette tip at block 110 at a flow rate in a range of about 1 µL/s to about 100 mL/s, such as, for example, in a range of about 1 µL/s to about 100 µL/s, about 5 µL/s to about 40 µL/s, about 50 µL/s to about 500 µL/s, 5 µL/s to about 400 µL/s, about 100 µL/s to about 300 µL/s, about 300 µL/s to about 700 µL/s, or about 1 mL/s to about 100 mL/s. In some embodiments, a gas may be aspirated into a pipette tip at block 110 at a flow rate of about 100, 200, 300, 400, 500, 600, 700, 800, 900 µL/s or more. The flow rates provided herein for aspirating a gas into a pipette tip are examples and are not intended to limit the scope of the invention. For example, the flow rate for aspirating a gas into a pipette tip may be less than 1 µL/s or greater than 100 mL/s.

Any suitable volume of gas may be aspirated into the pipette tip at block 110 at any suitable rate of aspiration. In some embodiments, a known volume of gas may be aspirated into the pipette tip at block 110. In some embodiments, the volume of gas aspirated into the pipette tip at block 110 may be in a range of about 1 µL to about 500 mL, such as, for example, in a range of about 5 µL to about 500 µL, about 25 µL to about 150 about 200 µL to about 500 µL, about 400 µL to about 1 mL, about 1 mL to about 5 mL, or about 10 mL to about 500 mL. In some embodiments, the volume of gas aspirated into the pipette tip at block 110 may be about 10, 20, 30, 40, 50, 60, 70, 80, 90, 100, 150, 200, 250, 300, 350, 400 μL or more. The volumes provided herein for aspirating a gas into the pipette tip are examples and are not intended to limit the scope of the invention. For example, the volume of gas aspirated into a pipette tip may be less than 1 μL or greater than 500 mL.

Some embodiments include collecting pressure data at block 120. In some embodiments, pressure data may be collected while aspirating gas into the pipette tip attached to the pipette at block 110 and/or while measuring a pipette pressure at block 100. In some embodiments, the pressure data may include the plurality of pipette pressure values measured at an internal portion of the pipette, as described in regard to block 100. In some embodiments, the plurality of pipette pressure values may include a maximum pressure value and a minimum pressure value. The maximum pressure value and minimum pressure value may occur at any point in a given time interval. For example, in some embodiments, the maximum pressure value may be measured at a first point in time and the minimum pressure value may be measured at a second point in time and the first point in time may be before the second point in time. In some embodiments, the maximum pressure value may be measured at a first point in time and the minimum pressure value may measured at a second point in time and the second point in time may be before the first point in time.

In some embodiments, the pressure data collected at block 120 may be collected prior to aspirating a liquid into the pipette tip. Thus, in some embodiments, only a gas may be present in the pipette tip while pressure data is collected at block 120 and/or while a pipette pressure is being measured at block 100.

Some embodiments include estimating a pressure range value at block 130. Some embodiments include using the collected pressure data at block 120 to estimate the pressure range value at block 130. In some embodiments, the pressure range value may be estimated at block 130 using two pressure values. Some embodiments include estimating the pressure range value at block 130 using a maximum pressure value and a minimum pressure value from the plurality of pipette pressure values generated at block 100. Some embodiments include estimating the difference between the maximum pressure value and the minimum pressure value to estimate the pressure range value at block 130. In some embodiments, estimating the pressure range value at block 130 includes subtracting the minimum pressure value from the maximum pressure value to obtain the pressure range value.

Some embodiments include determining and/or detecting if the pipette tip is properly functioning at block 140. In some embodiments, determining and/or detecting if the pipette tip is properly functioning at block 140 may include comparing the pressure range value to a threshold, such as, for example, 1, 2, 3, 4, or more thresholds. Some embodiments include comparing the pressure range value to two thresholds, such as, for example, a lower threshold and an upper threshold. Some embodiments include a threshold that may depend on and/or be tuned based on the pipette, the volume of fluid (i.e., liquid and/or gas) present in a pipette tip, the rate of aspiration or dispense, and/or the fluid type and/or properties thereof. In some embodiments, a threshold may be empirically determined.

In some embodiments, a threshold may be determined using any suitable rate of aspiration. In some embodiments, a threshold may be determined with a rate of aspiration in a range of about 1 μL/s to about 100 mL/s, such as, for example, in a range of about 1 μL/s to about 100 μL/s, about 5 μL/s to about 40 μL/s, about 100 μL/s to about 1 mL/s, about 300 μL/s to about 700 μL/s, or about 1 mL/s to about 100 mL/s. In some embodiments, a threshold may be determined with a rate of aspiration of about 100, 200, 300, 400, 500, 600, 700, 800, 900 μL/s or more. The rates of aspiration for determining a threshold provided herein are examples and are not intended to limit the scope of the invention. For example, the rate of aspiration for determining a threshold may be less than 1 μL/s or greater than 100 mL/s. The rate of aspiration for determining a threshold may be the rate at which a gas is aspirated into a pipette tip attached to a pipette. In some embodiments, a threshold is determined with a rate of aspiration that is the same as the rate at which a pipette aspirates gas into a pipette tip at block 110.

Some embodiments include, responsive to the pressure range value being greater than or equal to a lower threshold and the pressure range value being less than or equal to an upper threshold, determining that the pipette tip attached to the pipette is properly functioning at block 140. In some embodiments, responsive to determining that the pipette tip attached to the pipette is properly functioning at block 140, it may be determined that the pipette tip attached to the pipette is suitable for use. In some embodiments, determining that the pipette tip is suitable for use includes determining that the pipette tip attached to the pipette is suitable to aspirate and dispense a liquid. Some embodiments include aspirating a liquid into the pipette tip, responsive to determining that the pipette tip attached to the pipette is properly functioning at block 140.

In some embodiments, responsive to the pressure range value being less than a lower threshold, it may be determined that the pipette tip attached to the pipette is not properly functioning at block 140. In some embodiments, responsive to the pressure range value being greater than an upper threshold, it may be determined that the pipette tip attached to the pipette is not properly functioning at block 140. Some embodiments include removing the pipette tip from the pipette, responsive to determining that the pipette tip attached to the pipette is not properly functioning at block 140.

Some embodiments include determining that the pipette tip is defective, clogged, and/or improperly attached to the pipette, responsive to determining that the pipette tip attached to the pipette is not properly functioning at block 140. A defective pipette tip may include a pipette tip that is clogged (partially or fully), has a manufacturing defect, does not allow sufficient air flow through, does not contain a filter, is cracked, is punctured, and/or does not form an air-tight seal with the pipette. In some embodiments, a defective pipette tip and/or a pipette tip without a filter may be detected, responsive to determining that the pressure range value is less than a threshold, such as, for example, a lower threshold. In some embodiments, a defective pipette tip and/or a clogged pipette tip may be detected, responsive to determining that the pressure range value is greater than a threshold, such as, for example, an upper threshold.

Figure 6:
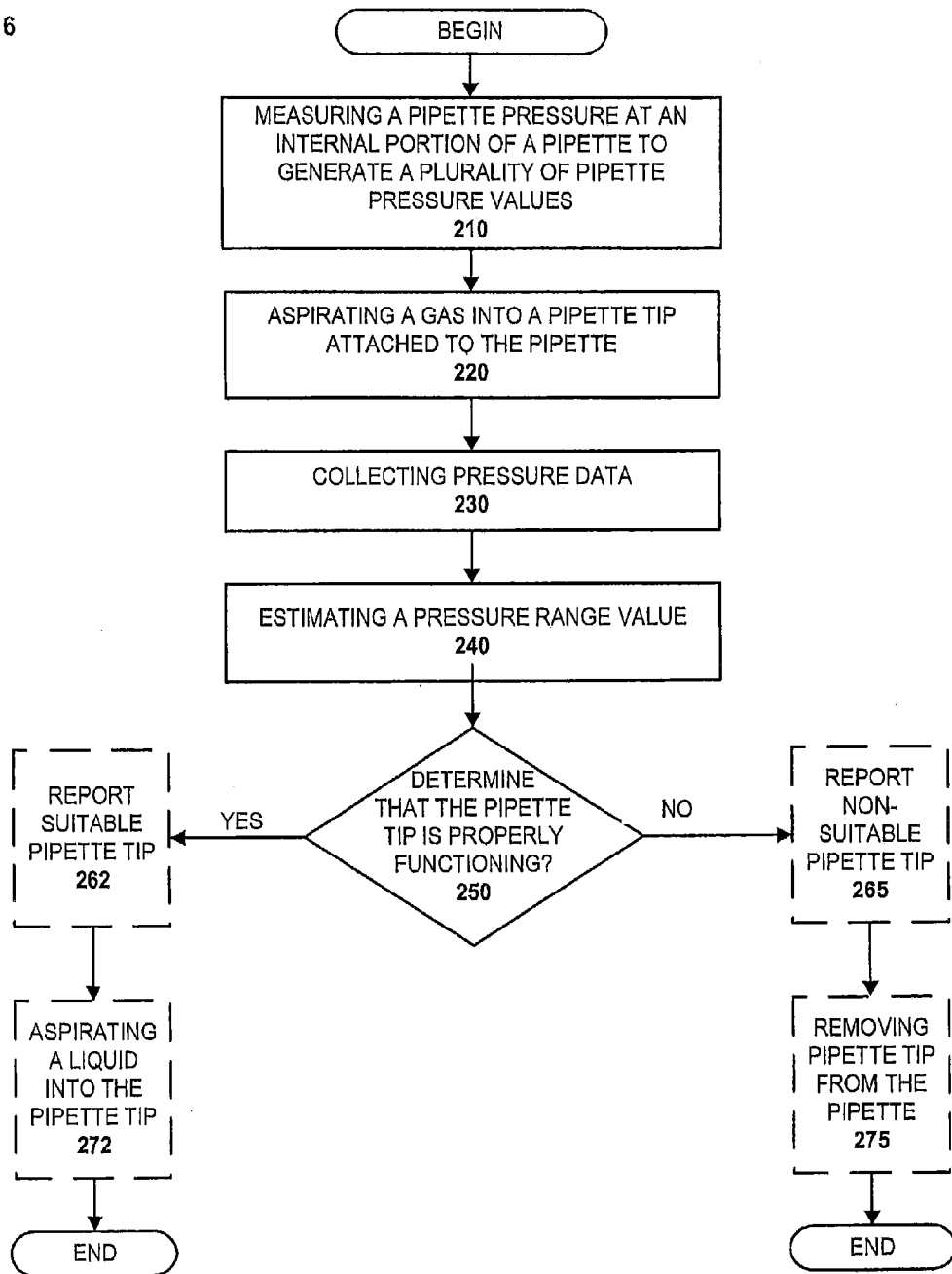
FIG. 6 is a flowchart illustrating operations in systems according to some embodiments of the present inventive subject matter.

Reference is now made to FIG. 6, which is a flowchart illustrating operations in systems according to some embodiments of the present inventive subject matter. The operations in the systems may include measuring a pipette pressure at an internal portion of a pipette to generate a plurality of pipette pressure values at block 210, aspirating a gas into a pipette tip attached to the pipette at block 220, collecting pressure data at block 230, and/or estimating a pressure range value at block 240. Each of these operations may be as described above in reference to FIG. 5 and duplicate discussion thereof may be omitted herein for the purpose of discussing FIG. 6.

Figure 7:
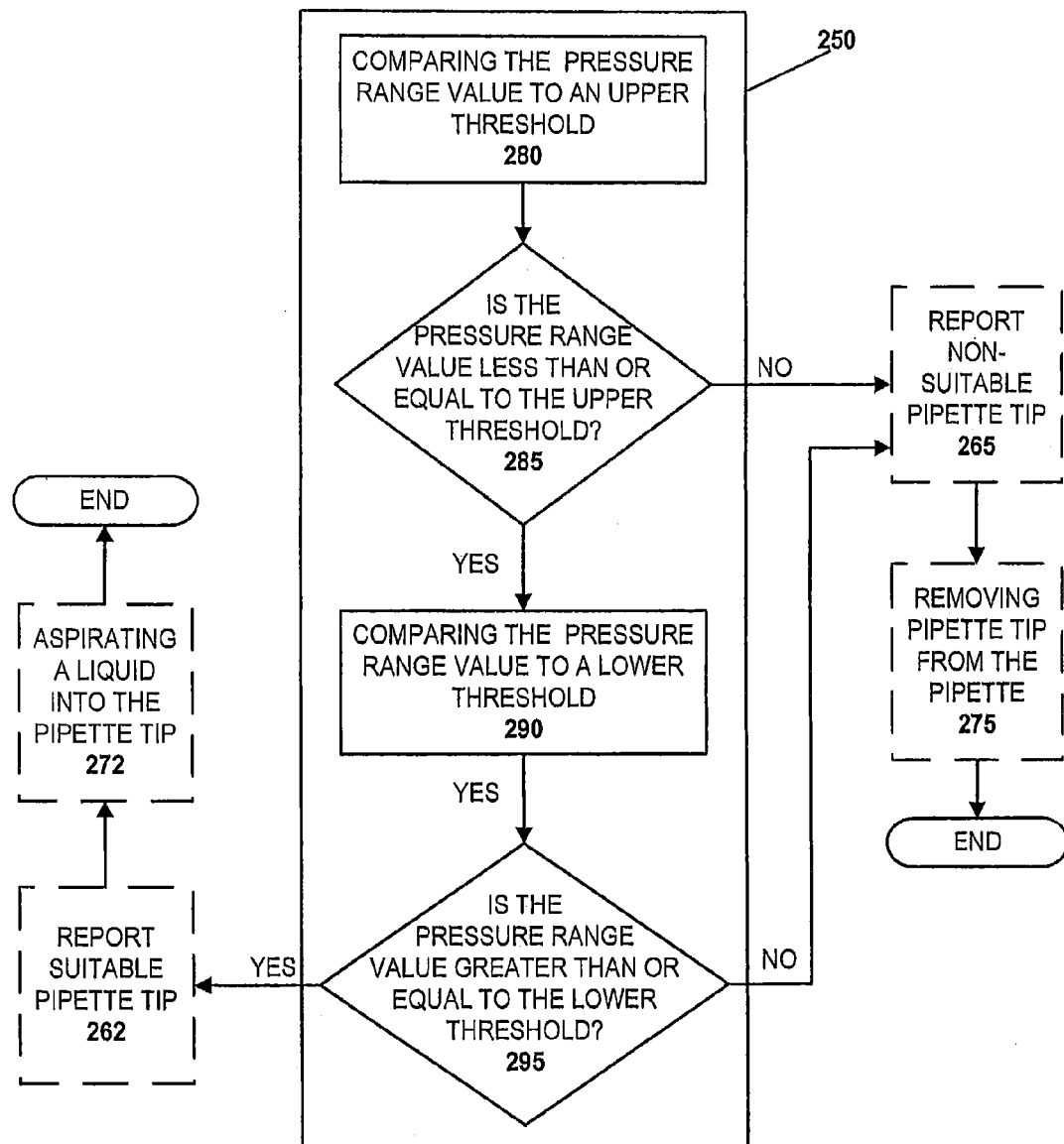
FIG. 7 is a flowchart illustrating operations in systems according to some embodiments of the present inventive subject matter.

In some embodiments, responsive to estimating a pressure range value at block 240, it may be detected and/or determined if the pipette tip is properly functioning at block 250. Detecting and/or determining if the pipette tip is properly functioning at block 250 may include several additional operations. For example, referring briefly to FIG. 7, which illustrates additional operations for detecting and/or determining if the pipette tip is properly functioning at block 250, in some embodiments, the operations at block 250 may include comparing the pressure range value to a threshold. Some embodiments include comparing the pressure range value to an upper threshold at block 280. In some embodiments, it may be determined if the pressure range value is less than or equal to the upper threshold at block 285. If the pressure range value is greater than the upper threshold, then a system may report a non-suitable pipette tip at block 265 and/or remove the pipette tip from the pipette at block 275. Some embodiments include comparing the pressure range value to a lower threshold at block 290, which may be responsive to determining that the pressure range value is less than or equal to the upper threshold at block 285. In some embodiments, it may be determined if the pressure range value is greater than or equal to the lower threshold at block 295. If the pressure range value is less than the lower threshold, then a system may report a non-suitable pipette tip at block 265 and/or remove the pipette tip from the pipette at block 275. If the pressure range value is greater than or equal to the lower threshold, then a system may report a suitable pipette tip at block 262 and/or aspirate a liquid into the pipette tip at block 272.

Referring again to FIG. 6, in some embodiments, if it is determined that the pipette tip is not properly functioning at block 250, then a system may report that the pipette tip is non-suitable at block 265. In some embodiments, a report that the pipette tip is non-suitable at block 265 may indicate that the pipette tip is not suitable for use and/or defective. Some embodiments include removing the pipette tip from the pipette at block 275 responsive to determining that the pipette tip is not properly functioning at block 250. In some embodiments, upon determining that the pipette tip is not properly functioning at block 250, then a system may stop performing the operations.

In some embodiments, if it is determined that the pipette tip is properly functioning at block 250, then a system may report that the pipette tip is suitable at block 262. In some embodiments, a report that the pipette tip is suitable at block 262 may indicate that the pipette tip is suitable for use and/or not defective. Some embodiments include aspirating a liquid into the pipette tip at block 272 responsive to determining that the pipette tip is properly functioning at block 250. In some embodiments, upon determining that the pipette tip is properly functioning at block 250, then a system may stop performing the operations.

During one or more operations described in regard to FIG. 6, the system may be acting at one or more of the same and/or different operations. In some embodiments, one or more operations may be occurring at any given time.

Figure 8:
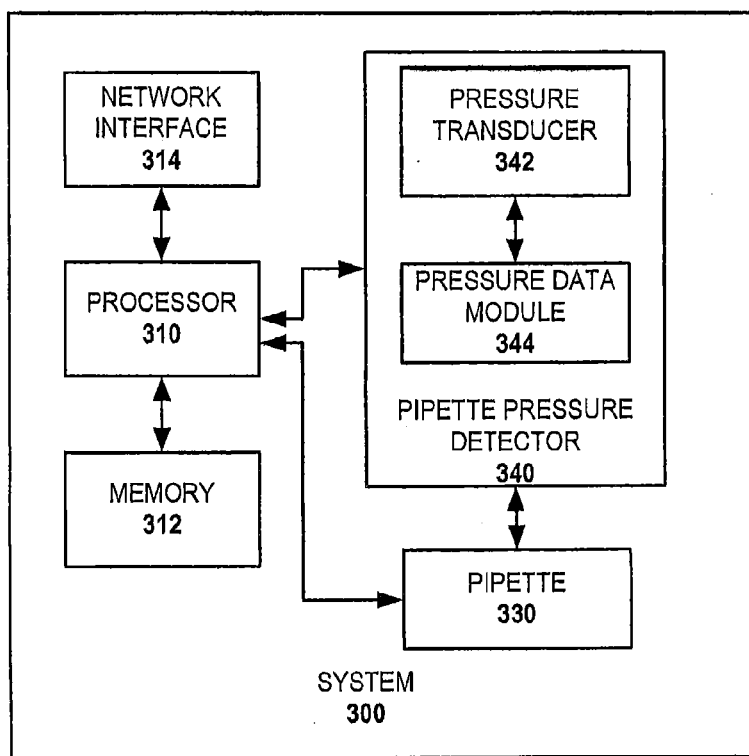
FIG. 8 is a block diagram illustrating systems according to some embodiments of the present inventive subject matter.

Reference is now made to FIG. 8, which is a block diagram illustrating a system 300 according to some embodiments of the present inventive subject matter. The system may include a processor 310, a memory 312, a network interface 314, a pipette 330, a pipette pressure detector 340, a pressure transducer 342, and pressure data module 344.

The processor 310 may be configured to execute computer program code from memory 312, described below as a computer readable storage medium, to perform at least some of the operations and methods described herein, and may be any conventional processor(s), including, but not limited to the AMD Athlon™ 64, or Intel® Core™ Duo, among others. The memory 312 may be coupled to the processor 310 and may include computer readable program code embodied therein that, when executed by the processor 310, may cause the processor 310 to receive, generate, store, and/or transmit information relating to an internal pressure in the pipette 330 and/or the location of the pipette 330 (e.g., if the pipette is in contact with a surface) and/or a condition of a pipette tip (e.g., pipette tip integrity, if a pipette tip is functioning properly, dispensing of a fluid from a pipette tip, if a droplet is at the distal end of the pipette tip, if the pipette tip is clogged, and/or if the pipette tip is empty).

In some embodiments, the pipette 330 may include a pipette tip, which may be releasably attached to the pipette 330. The pipette 330 may be in electronic communication with the processor 310. The pipette pressure detector 340 may include a pressure transducer 342 and a pressure data module 344. In some embodiments, the pressure transducer 342 and pressure data module 344 may be integrated into a single package. In some embodiments, the pipette pressure detector 340 may be mounted onto the pipette 330 and/or may be integral to the pipette 340.

The pressure transducer 342 may be in fluidic communication with the pipette 330 and/or may be built-in to the pipette 330. In some embodiments, the pressure transducer 342 may measure pressure and/or vacuum profiles at an internal portion of a pipette 330. The pressure transducer 342, pipette pressure detector 340, and/or pipette 330 may transmit real-time pressure data to the processor 310 and/or pressure data module 344 that may be communicatively coupled to the processor 310. The real-time pressure data may be used to detect a surface and/or to determine a position of the pipette 330 and/or a pipette tip attached to the pipette 330. The pressure data module 344 may receive and/or transmit signals corresponding to a pressure at an internal portion of the pipette 330. Some embodiments include the pressure data module 344 receiving signals from the pressure transducer 342. In some embodiments, the pressure data module 344 may convert a signal received from the pressure transducer 342 to a different signal and/or signal format, such as, for example, from an analog signal to a digital signal. In some embodiments, the pressure data module 344 may transmit signals to the processor 310. In some embodiments, the pipette 330, pipette pressure detector 340, pressure data module 344, and/or pressure transducer 342 may be programmable. The pipette 330, pipette pressure detector 340, pressure data module 344, and/or pressure transducer 342 may perform and/or be utilized in one or more operations of the methods and systems described above.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

Some embodiments provide that one or more of the programs may be executed during a portion of execution of another one of the programs in the corresponding process operation.

The flowchart and block diagrams in the figures illustrate the architecture, functionality, and operation of possible implementations of systems, methods and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The term "about," as used herein when referring to a measurable value, such as an amount or distance and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations off 20%, ±10%, ±5%, ±1%, ±0.5%, or even ±0.1% of X. A range provided herein for a measurable value may include any other range and/or individual value therein.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method comprising:
    collecting pressure data while aspirating a gas into a pipette tip attached to a pipette, the pressure data including a plurality of pressure values measured at an internal portion of the pipette and taken over a given time interval, the plurality of pressure values including a maximum pressure value and a minimum pressure value;
    estimating a pressure range value between the maximum pressure value and the minimum pressure value;
    responsive to the pressure range value being greater than or equal to a lower threshold and the pressure range value being less than or equal to an upper threshold, determining that the pipette tip attached to the pipette is properly functioning, or
    responsive to the pressure range value being less than a lower threshold or the pressure range value being greater than an upper threshold, determining that the pipette tip attached to the pipette is not properly functioning; and
    responsive to the pressure range value being greater than or equal to the lower threshold and the pressure range value being less than or equal to the upper threshold, determining that the pipette tip attached to the pipette is suitable for use, or
    responsive to the pressure range value being less than the lower threshold or the pressure range value being greater than the upper threshold, determining that the pipette tip is defective, clogged, and/or improperly attached to the pipette.

2. The method of claim 1, wherein collecting pressure data while aspirating the gas into the pipette tip attached to the pipette comprises measuring pipette pressure at given time intervals.

3. The method of claim 2, wherein aspirating the gas into the pipette tip attached to the pipette further comprises aspirating the gas into the pipette tip attached to the pipette over a given time interval.

4. The method of claim 1, wherein collecting pressure data while aspirating the gas into the pipette tip attached to the pipette comprises aspirating the gas at a given rate of aspiration.

5. The method of claim 4, wherein the given rate of aspiration is in a range of about 300 µL/sec to about 700 µL/sec.

6. The method of claim 1, wherein collecting pressure data while aspirating the gas into the pipette tip attached to the pipette comprises aspirating the gas prior to aspirating a liquid into the pipette tip.

7. The method of claim 1, wherein estimating the pressure range value between the maximum pressure value and the minimum pressure value comprises subtracting the minimum pressure value from the maximum pressure value to obtain the pressure range value.

8. The method of claim 1, wherein at least one of the upper threshold and the lower threshold is determined using a given rate of aspiration.

9. The method of claim 8, wherein the given rate of aspiration is in a range of about 300 µL/sec to about 700 µL/sec.

10. The method of claim 8, wherein the given rate of aspiration is the same as the rate of aspiration for aspirating the gas into the pipette tip attached to the pipette.

11. The method of claim 1, further comprising, responsive to the pressure range value being greater than or equal to the lower threshold and the pressure range value being less than or equal to the upper threshold, aspirating a liquid into the pipette tip.

12. The method of claim 1, further comprising, responsive to the pressure range value being less than the lower threshold or the pressure range value being greater than the upper threshold, removing the pipette tip from the pipette.

13. The method of claim 1, further comprising detecting that the pipette tip is defective or without a filter responsive to the pressure range value being less than the lower threshold.

14. The method of claim 1, further comprising detecting that the pipette tip is defective responsive to the pressure range value being greater than the upper threshold.

15. The method of claim 1, wherein the maximum pressure value is measured at a first point in time and the minimum pressure value is measured at a second point in time and the first point in time is before the second point in time.

16. The method of claim 1, wherein the maximum pressure value is measured at a first point in time and the minimum pressure value is measured at a second point in time and the second point in time is before the first point in time.

17. A computer system, comprising:
    a processor; and
    a memory coupled to the processor, the memory comprising computer readable program code embodied therein that, when executed by the processor, causes the processor to perform operations comprising the method of claim 1.

18. The computer system of claim 17, further comprising an apparatus for positioning a pipette and pipetting a liquid onto a surface of a target.

19. The computer system of claim 18, wherein the apparatus for positioning a pipette and pipetting a liquid onto a surface includes a pipette including a pipette pressure detector.

20. A computer program product comprising:
    a non-transitory computer readable storage medium having computer readable code embodied in the medium, the computer code comprising:
    computer readable code configured to perform operations comprising the method of claim 1.

* * * * *